US00PP26287P3

(12) United States Plant Patent
Caster et al.

(10) Patent No.: US PP26,287 P3
(45) Date of Patent: Jan. 5, 2016

(54) BLUEBERRY PLANT NAMED 'DRISBLUENINE'

(50) Latin Name: ***Vaccinium corymbosum* L.**
Varietal Denomination: DrisBlueNine

(71) Applicant: DRISCOLL STRAWBERRY ASSOCIATES, INC., Watsonville, CA (US)

(72) Inventors: Brian K. Caster, Salinas, CA (US); Arlen Draper, Payson, AZ (US); Jennifer K. Izzo, Watsonville, CA (US)

(73) Assignee: DRISCOLL STRAWBERRY ASSOCIATES, INC., Watsonville, CA (US)

( * ) Notice: Subject to any disclaimer, the term of this patent is extended or adjusted under 35 U.S.C. 154(b) by 182 days.

(21) Appl. No.: 13/998,114

(22) Filed: Oct. 2, 2013

(65) Prior Publication Data

US 2015/0096084 P1 Apr. 2, 2015

(51) Int. Cl.
*A01H 5/08* (2006.01)

(52) U.S. Cl.
USPC ..... Plt./157
CPC ..... *A01H 5/08* (2013.01)

(58) Field of Classification Search
USPC ..... Plt./157
See application file for complete search history.

*Primary Examiner* — June Hwu
(74) *Attorney, Agent, or Firm* — Jondle & Associates, P.C.

(57) ABSTRACT

A new and distinct variety of blueberry plant named 'DrisBlueNine' particularly distinguished by having a late harvest season, high productivity and large, firm berries, is disclosed.

2 Drawing Sheets

Genus and species: *Vaccinium corymbosum* L.
Variety denomination: 'DrisBlueNine'.

BACKGROUND OF THE NEW PLANT

The invention relates to a new and distinct blueberry variety designated 'DrisBlueNine' and botanically known as *Vaccinium corymbosum* L. This new blueberry variety was discovered in Clackamas County, Oreg. in August 2004 and originated from a cross between the proprietary female parent blueberry plant 'MS122' (unpatented) and the male parent blueberry plant 'G292' (unpatented). The original seedling of the new variety was first asexually propagated at a nursery in Monterey County, Calif. in 2004. 'DrisBlueNine' was subsequently asexually propagated and underwent further testing at a nursery in Santa Cruz County, Calif. for six years (2007-2012). The present invention has been found to be stable and reproduce true to type through successive asexual propagations via softwood cuttings.

Plant Breeder's Rights for this variety have not been applied for. 'DrisBlueNine' has not been made publicly available or sold more than one year prior to the filing date of this application.

SUMMARY OF THE INVENTION

The following are the most outstanding and distinguishing characteristics of this new cultivar when grown under normal horticultural practices in Santa Cruz County, Calif.

1. Late harvest season;
2. High productivity; and
3. Large, firm berries.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are four years old.

DESCRIPTION OF THE NEW CULTIVAR

Figure 1:
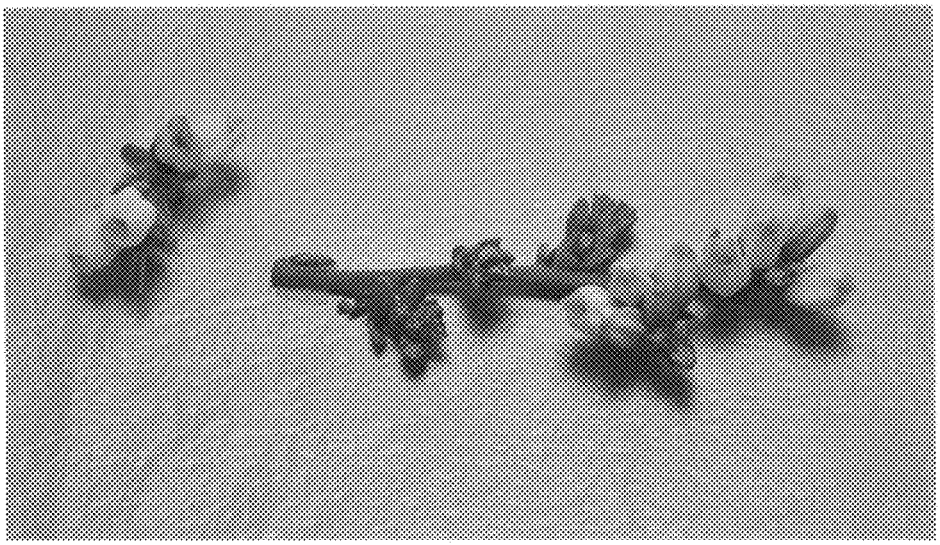
FIG. 1 shows a close-up of the mature flowers.
Figure 2:
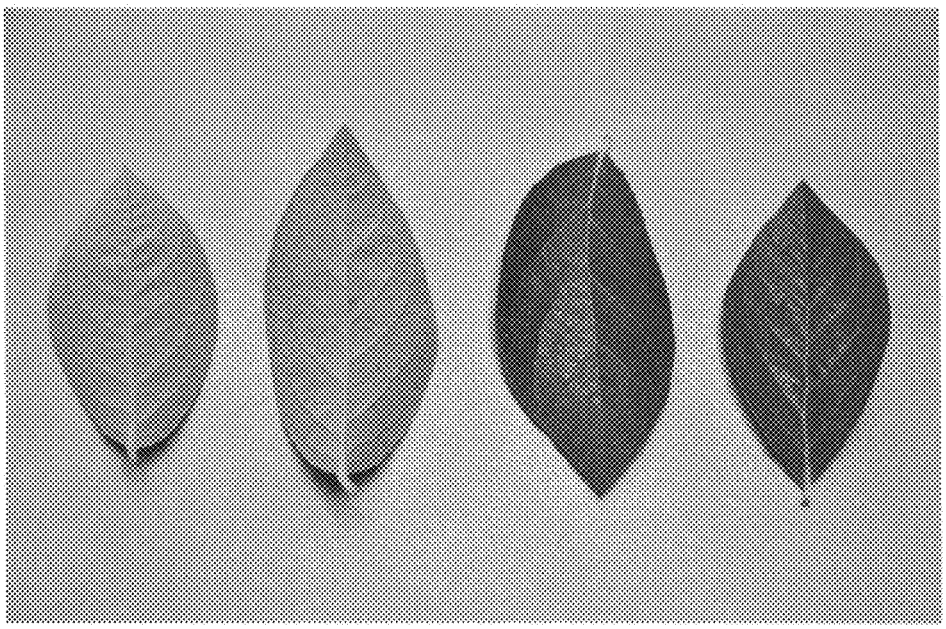
FIG. 2 shows a close-up of the leaves.
Figure 3:
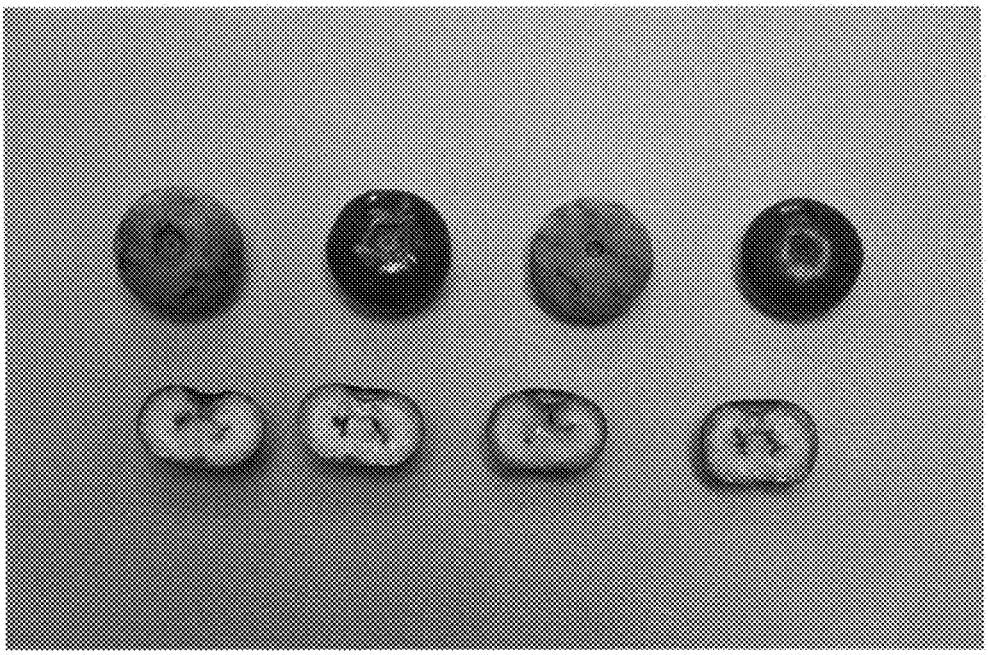
FIG. 3 shows a close-up of the whole fruit and a cross-section of the fruit.

The following detailed description sets forth the distinctive characteristics of 'DrisBlueNine.' The data which define these characteristics is based on observations taken in Santa Cruz County, Calif. from 2007-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueNine' has not been observed under all possible environmental conditions. The botanical description of 'DrisBlueNine' was taken from 4 year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION

Classification:

*Family.*—Ericaceae.
*Botanical.*—*Vaccinium corymbosum* L.
*Common name.*—Blueberry.
*Variety name.*—'DrisBlueNine'.

Parentage:

*Female parent*.—The proprietary blueberry plant 'MS122' (unpatented).

*Male parent*.—The blueberry plant 'G292' (unpatented).

Plant:

*Size*.—Small.

*Height*.—112.7 cm.

*Width*.—129.9 cm.

*Length/width ratio*.—0.9.

*Plant vigor*.—Strong.

*Growth habit*.—Semi-erect.

*Productivity*.—High.

*Cold hardiness*.—Medium; USDA Plant Hardiness Zone 7a.

*Chilling requirement*.—High.

*Propagation*.—Soft wood cuttings.

*Time of vegetative bud burst*.—Late.

*Fruiting type*.—Only on one-year-old shoots.

*Cane renewal*.—Medium.

*Internode length* (*upper half on one-year old shoot*).—47.7 mm.

*One-year old canes* (*young canes*).—Length: 104.3 cm. Diameter at the base: 8.8 mm. Diameter at the tip: 2.9 mm. Texture: Smooth. Color (One-year old shoot, branch and canes): RHS 146B (Medium yellow-green).

*Five-year old canes* (*mature canes*).—Length: 118.3 cm. Diameter at the base: 15.2 mm. Diameter at the tip: 4.2 mm. Texture: Rough. Color: RHS N200D (Light brown).

Leaves:

*Length*.—Long; 8.75 cm.

*Width*.—Medium; 4.4 cm.

*Length/width ratio*.—2.0; longer than broad.

*Shape*.—Elliptic.

*Apex*.—Acute.

*Base*.—Cuneate.

*Margin*.—Entire.

*Glossiness*.—Glossy.

*Pubescence*.—Glabrous (Absent).

*Sheath*.—Absent.

*Arrangement*.—Alternate.

*Venation*.—Reticulate.

*Color*.—Upper surface: Dark; RHS 137A (Dark green). Lower surface: Medium; RHS 148B (Medium yellow-green).

*Internode length* (*one-year old shoot, upper half*).—Long; 24.00 mm.

Petiole:

*Length*.—5.8 mm.

*Diameter*.—1.95 mm.

*Color*.—RHS 144C (Medium yellow-green).

Flowers:

*Length* (*excluding peduncle*).—Long; 9.94 mm.

*Diameter*.—6.91 mm.

*Length/width ratio*.—1.4.

*Color*.—RHS 157D (Light green-white).

*Flower bud*.—Length: 5.0 mm. Width: 3.0 mm. Number of flowers per bud: 6. Anthocyanin coloration: Medium; RHS 181A (Medium greyed-red). Color on immature buds: Medium; RHS 175C (Medium greyed-orange). Color on mature buds: Medium; RHS 142A (Medium green).

*Petal width*.—4.49 mm.

*Fragrance*.—Very faint or absent.

*Time of beginning flowering on one-year shoot*.—Late; Apr. 7, 2014 in Albany, Oreg.

*Time of flowering* (50% *full bloom*).—Late; Apr. 28, 2014 in Albany, Oreg.

*Pedicel*.—Length: 4.97 mm. Diameter: 1.06 mm. Color: RHS 142B (Medium green).

*Corolla*.—Aperture diameter: 3.54 mm. Shape: Urceolate (Urn-shaped). Size of corolla tube: Large. Corolla tube color: Medium; RHS 63A (Medium red-purple). Ridges on tube: Present.

*Peduncle length*.—17.51 mm.

Reproductive organs:

*Style length* (*including stigma*).—Medium; 16.68 mm.

*Style color*.—RHS 144C (Medium yellow-green).

*Ovary color*.—RHS 191B (Medium greyed-green).

*Pollen amount*.—Low.

*Pollen color*.—RHS 4D (Light yellow).

*Anther color*.—RHS 164A (Medium greyed-orange).

Fruit:

*Size*.—Large.

*Length*.—14.76 mm.

*Width*.—23.60 mm.

*Length/width ratio*.—0.6.

*Fruit pedicel diameter*.—1.10 mm.

*Weight*.—3.2 g.

*Number of berries per cluster*.—6.6.

*Cluster density*.—Medium.

*Shape in longitudinal sections*.—Oblate.

*Intensity of green color* (*immature fruit with bloom*).—Medium; RHS 143D (Medium green).

*Color of skin* (*immature fruit without bloom*).—RHS 59A (Dark red-purple).

*Color of skin* (*mature fruit without bloom*).—RHS 103A (Dark blue).

*Color of skin* (*mature fruit with bloom*).—RHS 98D (Light violet-blue).

*Intensity of bloom* (*mature fruit*).—Strong.

*Attitude of sepals*.—Incurving.

*Calyx*.—Diameter of basin: Large; 8.22 mm. Depth of basin: Deep; 4.32 mm. Diameter/depth ratio: 1.9.

*Flesh color*.—RHS 145D (Light yellow-green).

*Firmness*.—Firm.

*Sweetness*.—Low.

*Acidity*.—High.

*Time of beginning of fruit ripening* (*one-year old shoots*).—Late.

*Harvest season*.—Late.

*Harvest interval*.—Mid-July to early October.

Seeds:

*Length*.—1.92 mm.

*Width*.—1.12 mm.

*Length/width ratio*.—1.7.

*Abundance*.—Medium.

*Color*.—RHS 165A (Dark greyed-orange).

Resistance to pests and diseases: Data not available.

COMPARISON WITH PARENTAL AND COMMERCIAL VARIETIES

'DrisBlueNine' differs from the proprietary female parent 'MS122' (unpatented) in that 'DrisBlueNine' has a mid to high chill requirement, moderate vigor and light blue fruit, whereas 'MS122' has a low to mid chill requirement, high vigor and medium dark blue fruit.

'DrisBlueNine' differs from the male parent 'G292' in that 'DrisBlueNine' has moderate vigor and waxy (glaucous) leaves, whereas 'G292' has low vigor and green (non-glaucous) leaves.

'DrisBlueNine' differs from the commercial variety 'Elliott' (unpatented) in that 'DrisBlueNine' has a semi-erect growth habit and large berries, whereas 'Elliott' has an upright growth habit and medium sized berries.

'DrisBlueNine' differs from the commercial variety 'Bluecrop' (unpatented), in that 'DrisBlueNine' has a semi-erect growth habit, whereas 'Bluecrop' has an upright growth habit. Additionally, 'DrisBlueNine' has a late harvest season, whereas 'Bluecrop' has a mid-season harvest.

We claim:

1. A new and distinct variety of blueberry plant named 'DrisBlueNine' as shown and described herein.

* * * * *